United States Patent [19]

Aoki

[11] 4,198,977

[45] Apr. 22, 1980

[54] DENTAL THERAPEUTIC DEVICE

[75] Inventor: Yasuhiro Aoki, Hamamatsu, Japan

[73] Assignee: Teibow Company Limited, Hamamatsu, Japan

[21] Appl. No.: 882,075

[22] Filed: Mar. 1, 1978

[30] Foreign Application Priority Data

Dec. 15, 1977 [JP] Japan .................. 52-169306[U]

[51] Int. Cl.² ............... A61B 17/24; A61M 1/00;
      A61M 25/00; A61C 3/00
[52] U.S. Cl. ..................... 433/136; 128/760;
      128/296; 433/29
[58] Field of Search ........ 128/348, 2 G, 2 F, DIG. 5,
      128/350 R, 276; 32/34, 35, 40 R; 23/259;
      73/425.4 P, 421 R

[56] References Cited

U.S. PATENT DOCUMENTS

| | | | |
|---|---|---|---|
| 792,471 | 6/1905 | Smith | 132/89 |
| 982,232 | 1/1911 | Bartholomew | 132/93 |
| 2,902,146 | 9/1959 | Doherty | 73/425 |
| 3,599,679 | 8/1971 | Carter | 428/373 |
| 3,645,252 | 2/1972 | Gilford | 128/2 F |
| 3,767,520 | 10/1973 | Dick et al. | 428/398 |
| 3,771,536 | 11/1973 | Dragan | 132/89 |
| 3,887,741 | 6/1975 | Dwyer | 428/398 |
| 3,933,965 | 1/1976 | Gallone et al. | 428/398 |
| 4,023,559 | 5/1977 | Gaskell | 128/348 |
| 4,109,870 | 8/1978 | Wolber | 428/36 |
| 4,127,696 | 11/1978 | Okamoto | 428/373 |

*Primary Examiner*—Louis G. Mancene
*Assistant Examiner*—Michael J. Foycik, Jr.
*Attorney, Agent, or Firm*—Irving M. Weiner; Pamela S. Burt; Melvin Yedlin

[57] ABSTRACT

Disclosed is a device advantageously usable for dental therapy and examination, which is an elongated bundle of axially extending fibers. The elongated bundle is tapered at one or both of its ends, and the fibers are bonded to each other in places along their lengths so that the fiber bundle is coherent and the fibers define capillary passageways therebetween.

10 Claims, 13 Drawing Figures

Fig. 7
Fig. 8
Fig. 9
Fig. 10
Fig. 11　　Fig. 12　　Fig. 13
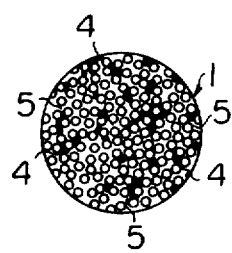 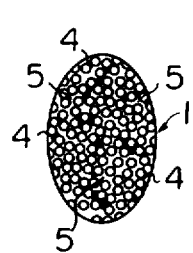 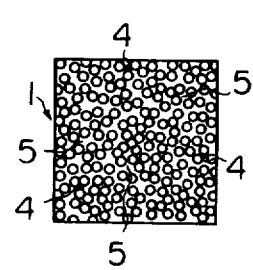

DENTAL THERAPEUTIC DEVICE

FIELD OF THE INVENTION

This invention relates to a device for dental therapy and examination. More particularly, the invention relates to a device useful for dental therapy, such as removal of blood, pus and the like, wiping and applying of medicine in a tooth cavity or root canal, and for dental examination such as bacilloscopy in a tooth cavity.

DESCRIPTION OF PRIOR ART

Conventionally, broach cottons and paper points have been utilized as a device for dental therapy and examination. The broach cottons are made by manually wrapping cotton fibers around the broach and then sterilizing it in a dry sterilizer. However, the broach cottons have drawbacks in that the cotton fibers tend to be retained in the root canal when they are used during a dental operation and it is difficult to produce the product under sanitary conditions even by sterilization. The paper points also have drawbacks in that the preparation thereof requires a great deal of skill and much time, and the points are poor in absorbing blood, pus, liquid medicine and the like.

SUMMARY OF THE INVENTION

It is the primary object of the present invention to provide a dental therapeutic and examination device of an excellent quality, which can be easily inserted into the root canal or tooth cavity without leaving fibers therein and which is excellent for absorbing blood, pus, liquid medicine and the like.

The object of the present invention can be attained by providing a device which comprises an elongated bundle of axially extending fibers, which elongated bundle is tapered at one or both of its ends and which fibers are bonded to each other in places along their lengths so that the fiber bundle is coherent and the fibers define capillary passageways therebetween.

Due to its simple construction, the device for dental therapy and examination of the present invention can be produced continuously and in large quantities by means of mechanical production and, therefore, can be provided inexpensively.

BRIEF DESCRIPTION OF THE DRAWINGS

FIGS. 1 through 10 are schematic front views of embodiments of the device of the present invention having various configurations.

FIGS. 11 through 13 are enlarged transverse cross-sectional views of embodiments of the device of the present invention, wherein the cross-sections are circular, oval and square, respectively.

DESCRIPTION OF PREFERRED EMBODIMENTS

Figure 1:
Figure 2:
Figure 3:
Figure 4:
Figure 5:
Figure 6:

Referring now to FIGS. 1 through 10, the device of the present invention may be prepared by axially a multiplicity of fibers in parallel, bonding the axially arranged fibers therebetween by means of an adhesive or surface dissolution or fusion to form a coherent elongated bundle 1, cutting the formed bundle to a prescribed length, tapering the cut bundle at one or both of the longitudinal ends into a conical shape 2 using, for example, a grinder, and then sterilizing it. The device of the present invention so prepared can have the following dimensions, for example, the outer diameter of the elongated bundle 1 being 0.8 mm, the length of the device being 27 mm and the outer diameter of the tapered longitudinal end 2 being 0.2 mm. If desired, the tapered longitudinal end 2 of the fiber bundle 1 may be formed into a globular shape 3, during the tapering process, as shown in FIGS. 2, 4, 6, 8 and 10.

For the fibers composing the elongated bundle, any animal, vegetable and synthetic fibers may be employed. However, synthetic fibers are preferred. Examples of synthetic fibers which can be advantageously used for the present invention are sliver-like or filamentary fibers, each having a fineness of about 3 to 20 denier, made of polyester, nylon, vinylon, polyacetal, polyurethane, polyethylene and the like. In the case of the filamentary fibers, it is desirable to employ textured fibers.

Where the fiber bundle is made coherent by an adhesive, it is advantageous that the adhesive be used in an amount as small as possible but sufficient to maintain the configuration of the fiber bundle in a coherent, elongated rod shape, in order to produce a gentle sensation when felt by a patient and to increase the fiber bundle's capacity for absorbing blood, pus, liquid medicine and the like, during a dental operation. As examples of a non-toxic adhesive which may be used for the present invention, there are thermoplastic synthetic resins such as acrylic, polystyrene, polycarbonate, polyacetal, polyvinyl chloride and ABS (acrylonitrile-butadiene-styrene) resins; thermosetting resins such as unsaturated polyester, melamine, phenolic, epoxide and poly-urethane resins; natural thickeners such as starch and casein; and CMC (carboxymethyl cellulose). As shown in FIGS. 11 through 13, in the obtained device, the adhesive 4 is present under a dotty condition existing between the fibers for making the fiber bundle coherent while forming, between the fibers, numerous fine openings 5 communicated together in the axial direction and allowing a rapid and smooth absorption of blood, pus, liquid medicine and the like due to the capillarity of the communicated openings. Naturally, the axially extending fibers are bonded to each other in places along their lengths.

When the elongated fiber bundle is formed using synthetic fibers, the bundle can be made to be coherent due to heat fusion of the fibers. In such a case, since the fibers are generally not straight and, therefore, the adjoining fibers are brought into contact with each other in places and not brought into contact in other places along their lengths, when the fibers have been axially arranged in parallel, a coherent elongated fiber bundle wherein the fibers are bonded to each other in places along their lengths and across the transverse cross-section of the fiber bundle, is heated to such an extent that only the regions of the fibers in contact with each other are fused and bonded. Then, the fiber bundle may be formed into an appropriate configuration and sterilized as mentioned above. The device thus obtained is made to be coherent through the fused and bonded regions of the component fibers while possessing numerous axially communicated fine openings between the fibers, which allow a rapid and smooth absorption of blood, pus, liquid medicine and the like.

It should be noted that the fiber bundle may be formed in such a condition that the fibers in the outer portion of the bundle are bonded while the fibers in the inner portion remain unbonded. Such construction of the device may be more preferable because an increased absorption capacity thereof can be attained. Furthermore, the dental therapeutic and examination device of the invention may have a transverse cross-section of a circular, oval, triangular, tetragonal or polygonal shape. The transverse cross-section may also be in an astral shape. It has been found that the device of the present invention exhibits a liquid absorption of from 40 to 60% based on the weight of the device, while conventional paper points exhibit in general a liquid absorption of only about 10%. It has also been found that the device of the invention can be thoroughly saturated with horse blood within 30 seconds but that conventional paper points can only be partially saturated with horse blood even for a period of 2 minutes.

The device for dental therapy and examination according to the invention has advantages in that it can be easily inserted into the interior of a root canal or tooth cavity without leaving any fibers therein, it has an excellent absorption capacity for blood, pus, liquid medicine and the like and it provides a gentle sensation when felt by a patient during a dental operation. The device of the present invention has further advantages in that it can be produced continuously and in large quantities by means of mechanical production and, thus, can be provided inexpensively under sanitary conditions.

What is claimed is:

1. A device for dental therapy and examination, comprising:
    an elongated, substantially rod-shaped, bundle of fibers;
    said elongated bundle of fibers being provided with at least one tapered end thereof for insertion into a tooth cavity or root canal;
    said bundle of fibers including a multiplicity of outer fibers and a multiplicity of inner fibers, said outer and inner fibers extending substantially in the axial direction of said bundle;
    said fibers of said multiplicity of inner and outer fibers being arranged in substantially axially-coextensive parallel relation to each other;
    said bundle of fibers being bonded to each other at intermittent portions along the lengths thereof to define a multiplicity of openings between said fibers, said multiplicity of openings forming capillary passageways which communicate together in the axial direction of said bundle for the absorption of liquids; and
    said multiplicity of outer fibers defining a substantially smooth and coherent outer surface portion of said bundle.

2. A device according to claim 1, wherein:
    said bundle of fibers are bonded to each other at intermittent portions along the lengths thereof by a non-toxic adhesive.

3. A device according to claim 1, wherein:
    said bundle of fibers are bonded to each other at intermittent portions along the lengths thereof by means of surface dissolution or fusion such that said multiplicity of fibers are bonded together in substantially intermittent longitudinally and transversely extending areas of said bundle.

4. A device according to claim 1, wherein:
    said bundle of fibers is bonded together only in the outer portion of said bundle defined by said multiplicity of outer fibers, while said multiplicity of inner fibers are unbonded.

5. A device according to claim 1, wherein:
    said tapered end has a substantially globular shape.

6. A device according to claim 1, wherein: said fiber bundle has a circular, oval, triangular, tetragonal or polygonal cross-section.

7. A device according to claim 1, wherein:
    said device is sterilized.

8. A device according to claim 1, wherein:
    said multiplicity of outer and inner fibers comprise synthetic filamentary textured fibers having a fineness of substantially 3 to 20 denier.

9. A device according to claim 1, wherein:
    said bundle of fibers has an outer diameter of approximately 0.8 mm, and a length of approximately 27 mm.

10. A device according to claim 1, wherein:
    said elongated bundle of fibers is substantially continuously tapered from a first end to a second end thereof, so as to define a substantially conical shape of said bundle of fibers.

* * * * *